United States Patent [19]
Wu

[11] Patent Number: 5,887,431
[45] Date of Patent: Mar. 30, 1999

[54] OIL CYLINDER FOR A STAND CARRIAGE

[76] Inventor: Kai-Ping Wu, 58, Ma Yuan West St., Taichung, Taiwan

[21] Appl. No.: 965,655

[22] Filed: Nov. 6, 1997

[51] Int. Cl.[6] .................................................. F15B 15/20
[52] U.S. Cl. ............................................... 60/477; 60/481
[58] Field of Search ............................. 60/477, 481, 482

[56] References Cited

U.S. PATENT DOCUMENTS

| | | | |
|---|---|---|---|
| 3,775,027 | 11/1973 | Craft | 60/477 |
| 4,144,713 | 3/1979 | Clark et al. | 60/477 |
| 4,487,019 | 12/1984 | Johansson | 60/481 |

Primary Examiner—Sheldon J. Richter

[57] ABSTRACT

An oil cylinder has a valve body, an oil pressure chamber, and an oil storage chamber. A shaft extends from the oil pressure chamber. The valve body has a piston chamber, an arc-shaped through hole, an enlarged hole receiving a rotating post, a first oil passage, a second oil passage, a third oil passage, a fourth oil passage, an oil hole, a first channel, and a second channel. A piston is disposed in the piston chamber. A trip lever passes through the arc-shaped through hole. The trip lever is connected to the rotating post. A big ball is placed in the third oil passage. A small ball is placed in the second oil passage. A compression spring is connected to the bolt and the big ball. A coiled spring is connected to the big ball and the small ball. A swivel rod is connected to the rotating post. A V-ring oil seal encloses the piston. An oil relief device is disposed on the valve body and inserted in the first channel.

6 Claims, 8 Drawing Sheets

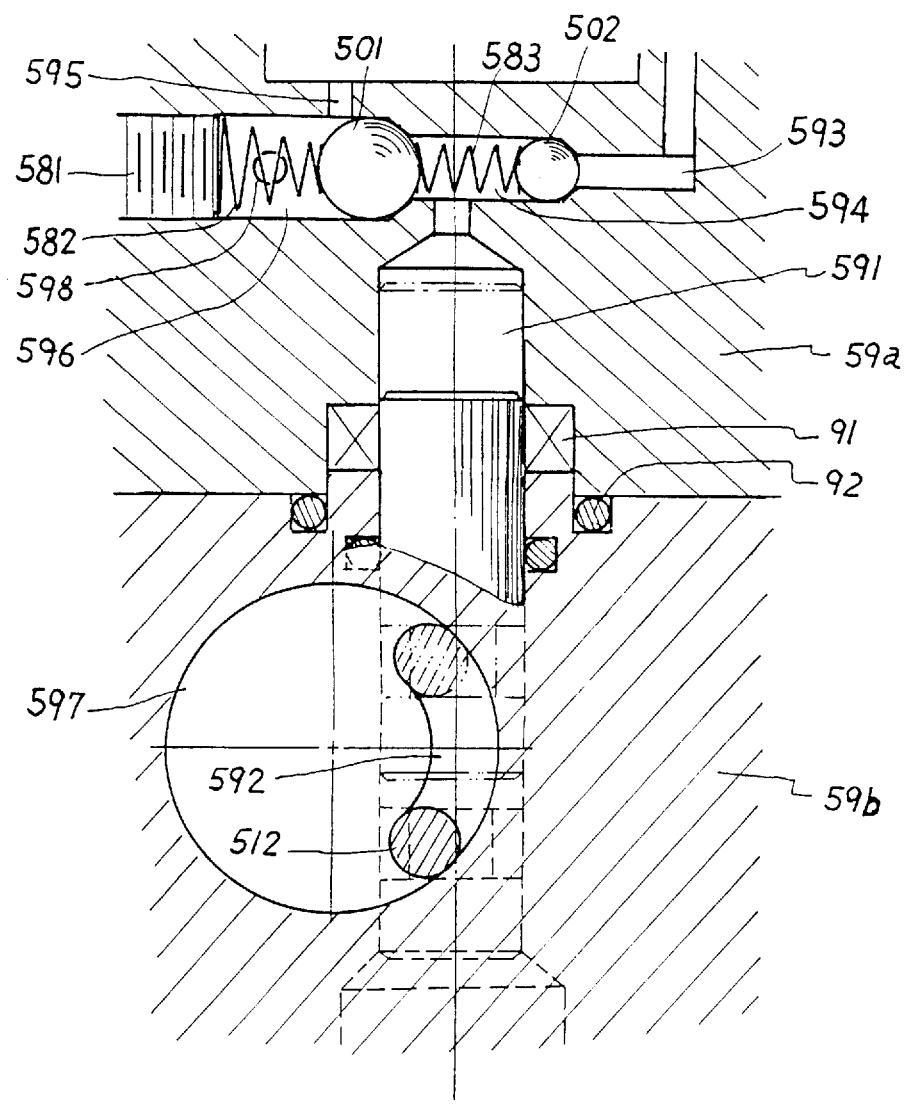
F I G. 5

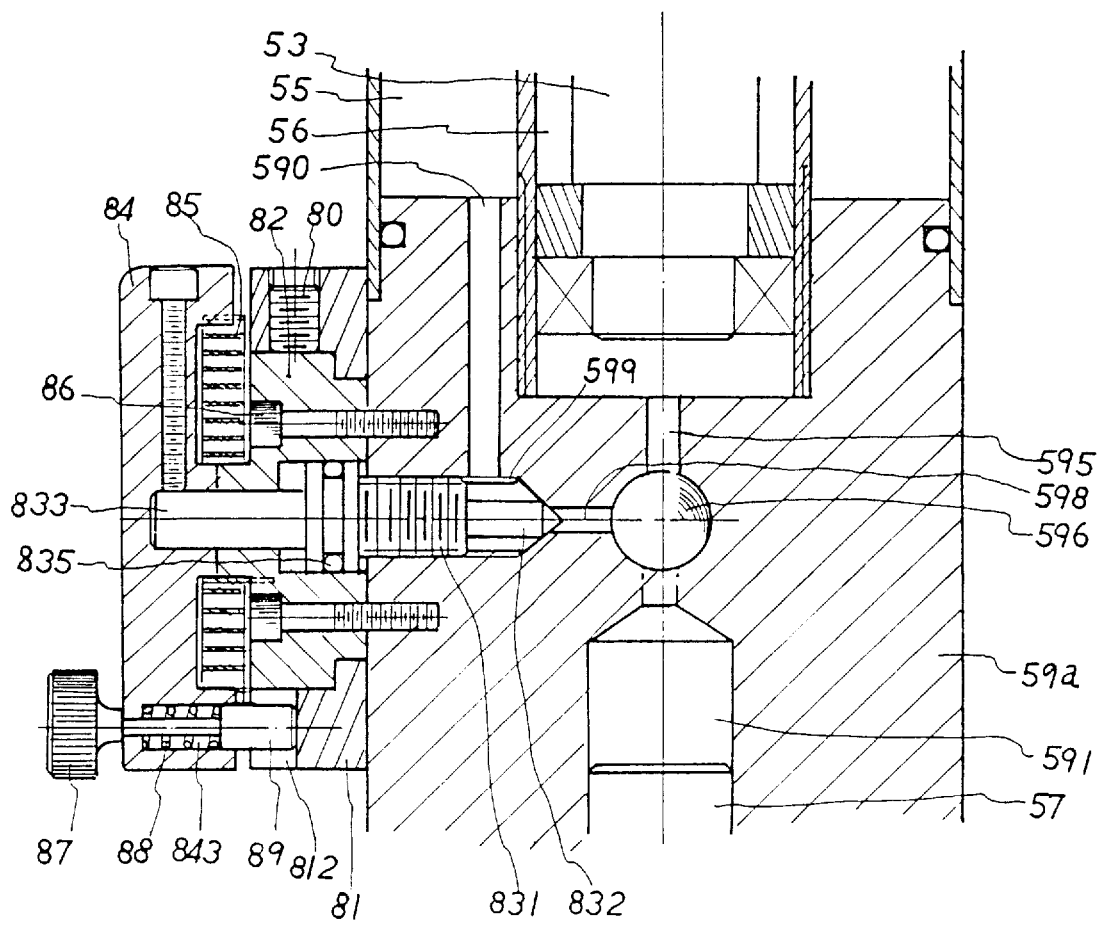
F I G. 6

5,887,431

OIL CYLINDER FOR A STAND CARRIAGE

BACKGROUND OF THE INVENTION

The present invention relates to an oil cylinder for a stand carriage. More particularly, the present invention relates to an oil cylinder for a stand carriage in a hospital.

Referring to FIGS. 1 to 3, a stand carriage comprises a U-shaped frame 1, four casters 6 connected to the U-shaped frame 1, a support frame 2 disposed on the 10 U-shaped frame 1, a bracket rod 3 disposed on the support frame 2, a support rod 54' disposed on the support frame 2 pivotally, an oil cylinder 5' disposed on the support rod 54', a shaft 53' extending from the oil cylinder 5' and connected to the bracket rod 3, and a button 52' disposed on the oil cylinder 5' to control the oil in the oil cylinder 5'. A hook device 4 is hung on the bracket rod 3. The oil cylinder 5' comprises a valve body 59', an oil pressure chamber 56', and an oil storage chamber 55'. A piston chamber 591' is disposed in the valve body 59'. A piston 57' is disposed in the piston chamber 591'. An annular groove 571' is formed on the piston 57'. An arc-shaped through hole 592' is formed in the valve body 59' communicating with the piston chamber 591'. A trip lever 512' passes through the arc-shaped through hole 592' and inserted in the annular groove 571'. An enlarged hole 597' is formed in the valve body 59' receiving a rotating post 511'. The trip lever 512' is connected to the rotating post 511' eccentrically. The rotating post 511' can be rotated in the enlarged hole 597' freely. A first oil passage 593' is formed in the valve body 59' communicating with the oil storage chamber 55'. A second oil passage 594' is formed in the valve body 59' communicating with the first oil passage 593'. A third oil passage 596' is formed in the valve body 59' communicating with the second oil passage 594'. A fourth oil passage 595' is formed in the valve body 59' communicating with the oil pressure chamber 56'. A big ball 501' is placed between the third oil passage 596' and the second oil passage 594'. A small ball 502' is placed between the second oil passage 594' and the first oil passage 593'. A bolt 581' is inserted in the third oil passage 596'. A compression spring 582' is connected to the bolt 581' and the big ball 501'. A coiled spring 583' is connected to the big ball 501' and the small ball 502'. The big ball 501 ' seals a first end of the second oil passage 594'. The small ball 502' seals a second end of the second oil passage 594'. The second oil passage 594' communicates with the piston chamber 591'. A swivel rod 51' is connected to the rotating post 511'. When the swivel rod 51' is operated, the rotating post 511' drives the trip lever 512' to move reciprocally. Therefore, the piston 57' can move upward and downward alternately. When the piston 57' moves downward, the oil in the oil storage chamber 55' flows into the first oil passage 593'. The small ball 502' is forced to move leftward so that the oil can flow into the piston chamber 591'. When the piston 57' moves upward, the oil in the piston chamber 591' flows into the third oil passage 596', the fourth oil passage 595', and the oil pressure chamber 56'. Since the shaft 53' extends from the oil pressure chamber 56', the shaft 53' will move upward to lift the bracket rod 3. An O-ring oil seal (not shown in the figures) is disposed in the piston chamber 591'. An oil hole 598' in the valve body 59' communicates with the third oil passage 596'. A steel ball (not shown in the figures) seals an end of the oil hole 598'. However, the O-ring oil seal cannot prevent the leakage of oil effectively. A V-ring oil seal can prevent the leakage oil effectively. Since the piston chamber 591' is very narrow, a V-ring oil seal cannot be disposed in the piston chamber 591'. Furthermore, the piston chamber 591' is too narrow and too deep to be fabricate precisely. Therefore, the motion of the piston 57' will be influenced. The operation of the oil cylinder 5' will be influenced also.

SUMMARY OF THE INVENTION

An object of the present invention is to provide an oil cylinder for a stand carriage in order to control a lift motion of the stand carriage precisely.

Another object of the present invention is to provide an oil cylinder which has two halved valves to form a complete valve body so that the manufacture of the oil cylinder is simplified.

Another object of the present invention is to provide an oil cylinder which has a V-ring oil seal to prevent the leakage of oil from the piston chamber effectively.

Accordingly, an oil cylinder comprises a valve body, an oil storage chamber disposed on the valve body, and an oil pressure chamber disposed in the oil storage chamber. A piston chamber is disposed in the valve body. The valve body has a first half valve and a second half valve coupled with the first half valve. The first half valve and the second half valve are fastened by at least a fastener. A shaft extends from the oil pressure chamber. A piston is disposed in the piston chamber. An annular groove is formed on the piston. An arc-shaped through hole is formed in the valve body communicating with the piston chamber. A trip lever passes through the arc-shaped through hole and inserted in the annular groove. An enlarged hole is formed in the valve body receiving a rotating post. The trip lever is connected to the rotating post eccentrically. A first oil passage is formed in the valve body communicating with the oil storage chamber. A second oil passage is formed in the valve body communicating with the first oil passage. A third oil passage is formed in the valve body communicating with the second oil passage. A fourth oil passage is formed in the valve body communicating with the oil pressure chamber. A big ball is placed in the third oil passage. A small ball is placed in the second oil passage. A bolt is inserted in the third oil passage. A compression spring is connected to the bolt and the big ball. A coiled spring is connected to the big ball and the small ball. The big ball seals a first end of the second oil passage. The small ball seals a second end of the second oil passage. The second oil passage communicates with the piston chamber. A swivel rod is connected to the rotating post. A V-ring oil seal encloses the piston. An oil ring is disposed between the first half valve and the second half valve. An oil hole is formed in the valve body communicating with the third oil passage. A first channel is formed in the valve body communicating with the oil hole. A second channel is formed in the valve body communicating with the first channel. An oil relief device is disposed on the valve body and inserted in the first channel. The oil relief device comprises an annular seat, a hollow disk inserted in the annular seat, a spiral power spring disposed on the hollow disk, a swivel button enclosing the spiral power spring, a control rod passing through the swivel button, a pull button having a hollow post inserted in the swivel button and receiving a threaded end of the control rod, an elastic member disposed between the hollow post and a cylinder head of the control rod, and a needle valve having a sleeve passing through the hollow disk and the spiral power spring and inserted in the swivel button, an annular recess receiving an oil gasket, a threaded portion inserted in the hollow disk, and a cone-shaped end inserted in the first channel. The annular seat has a threaded hole receiving a stud, a block face, a recess portion abutting the block face, an inclined groove portion abutting the recess portion, and a center hole receiving the hollow disk. The hollow disk has a circular central hole receiving the oil gasket and a circular central aperture receiving the sleeve. The circular central aperture communicates with the circular central hole. The swivel button has a central recess hole receiving the sleeve, a round hole, and a round aperture communicating with the round hole. The elastic member encloses the threaded end of the control rod. The threaded end of the control rod is inserted in the round aperture. The cylinder head of the control rod is inserted in the round hole.

BRIEF DESCRIPTION OF THE DRAWINGS

FIG. 5 is a partially sectional view of an oil cylinder of a preferred embodiment in accordance with the present invention;

FIG. 6 is a sectional view illustrating an oil relief device disposed in the oil cylinder;

DETAILED DESCRIPTION OF THE INVENTION

Figure 1:
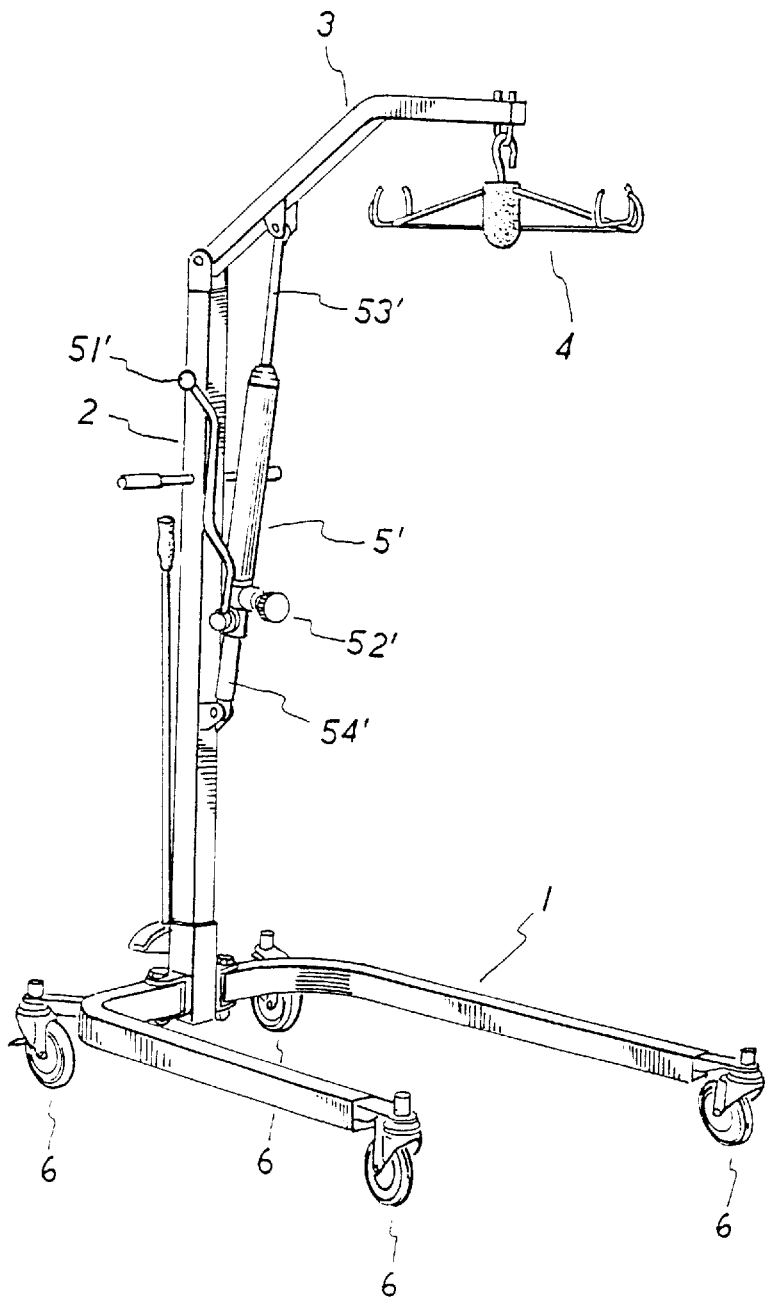
FIG. 1 is a perspective view of a stand carriage of the prior art.
Figure 2:
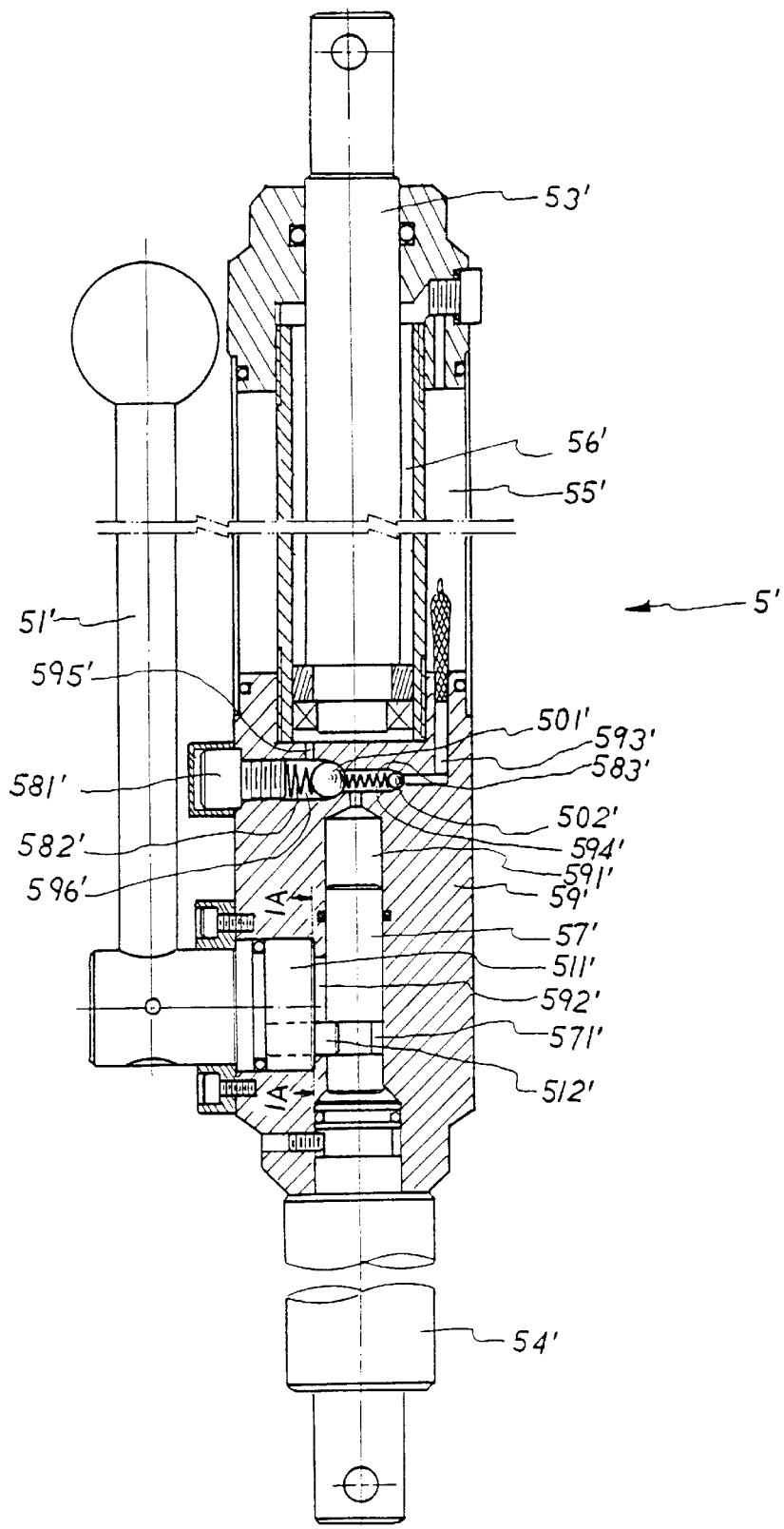
FIG. 2 is a sectional view of a conventional oil cylinder of the prior art.
Figure 3:
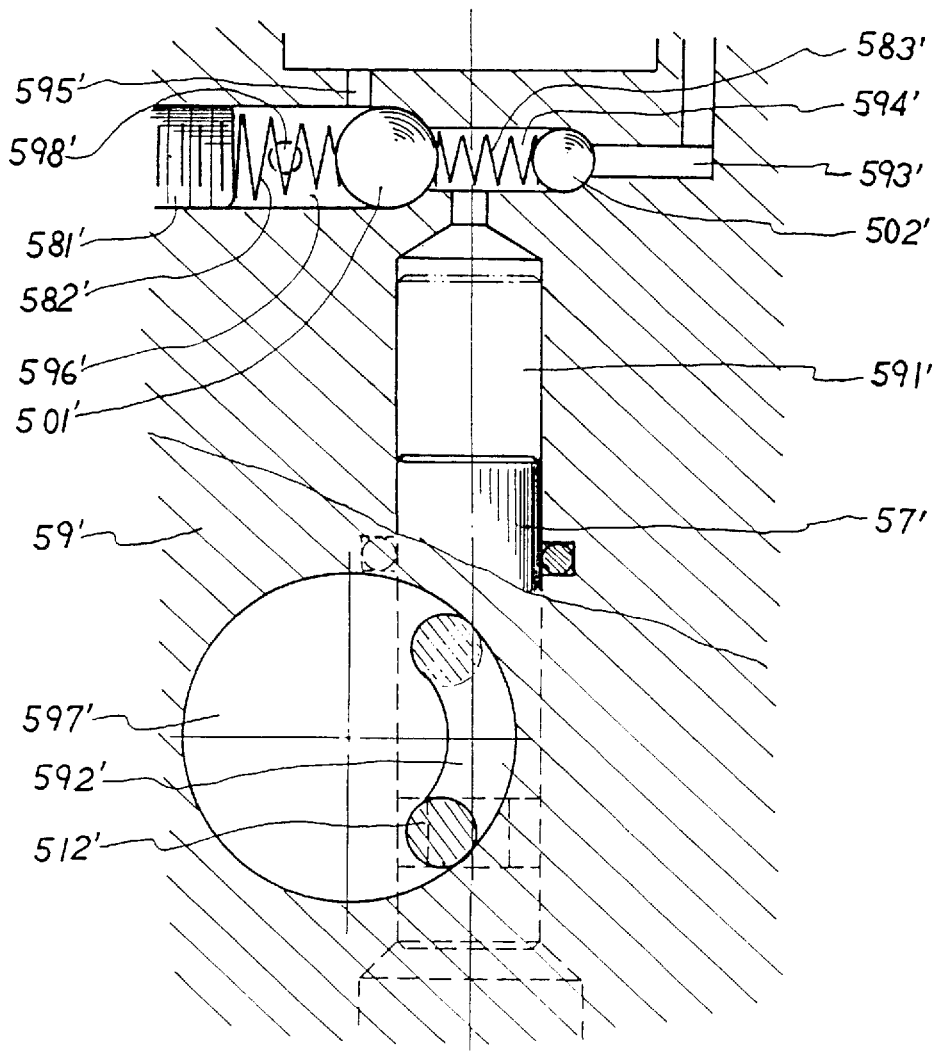
FIG. 3 is a sectional view taken along line 1A—1A in FIG.2.
Figure 4:
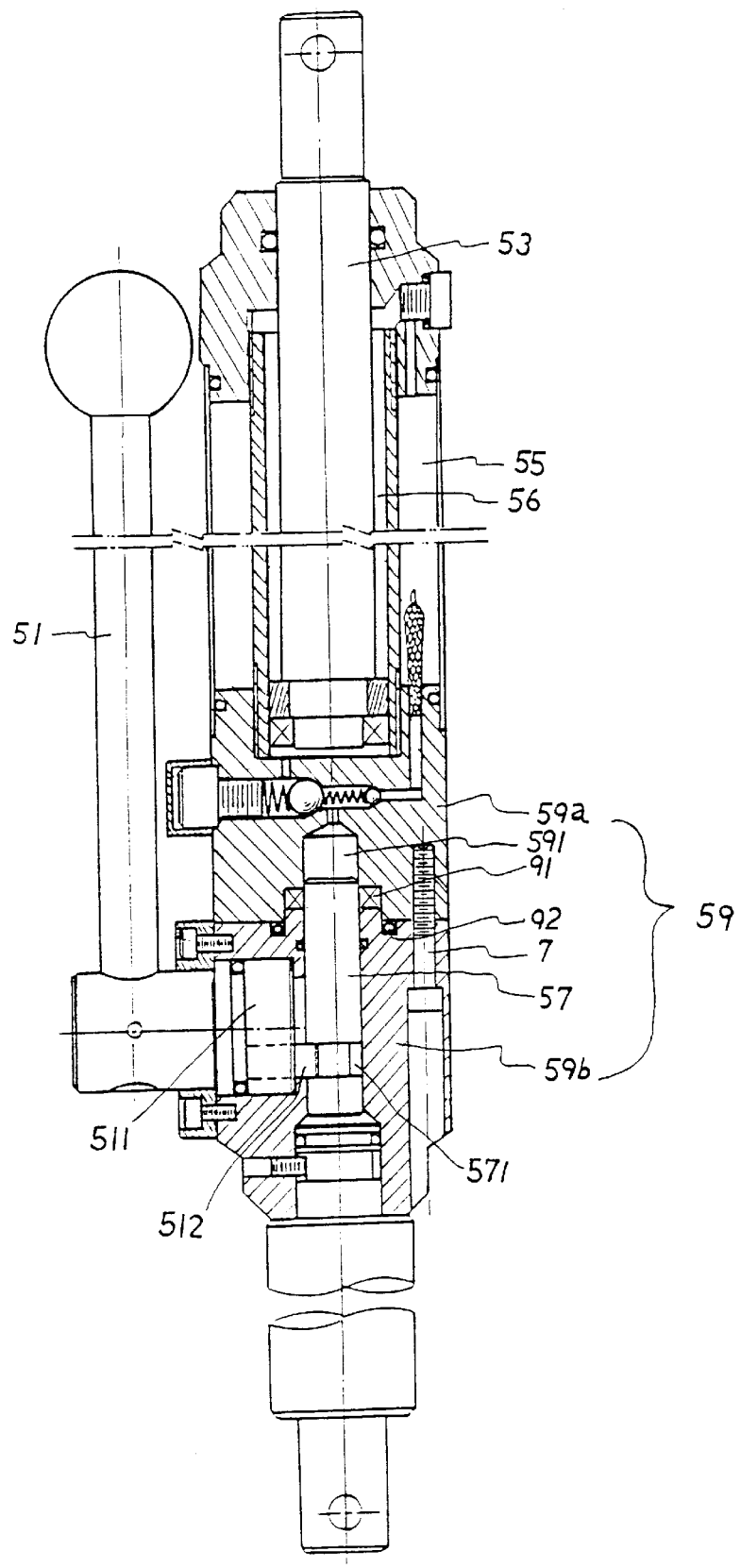
FIG. 4 is a sectional view of an oil cylinder of a preferred embodiment in accordance with the present invention.
Figure 7:
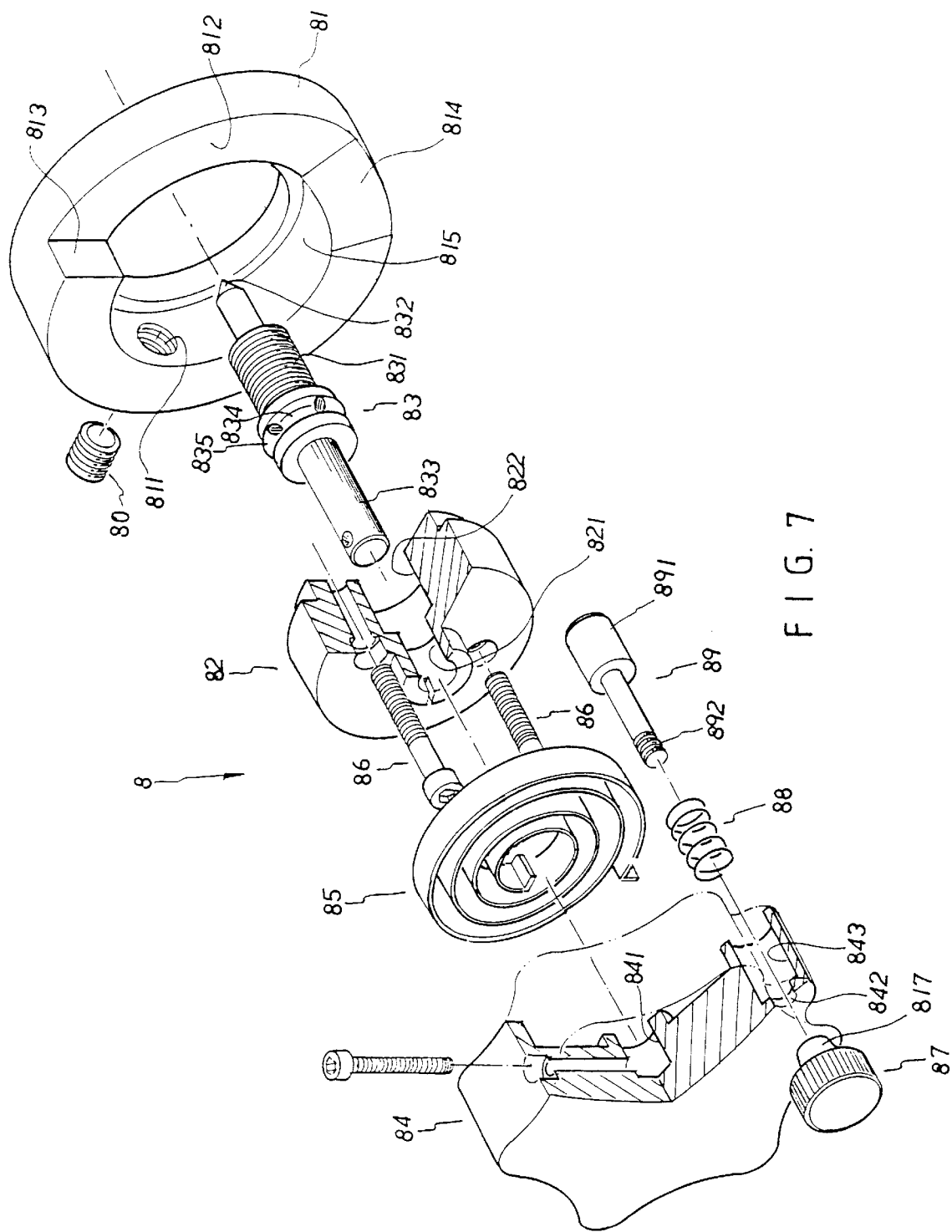
FIG. 7 is a perspective exploded view of an oil relief device of a preferred embodiment in accordance with the present invention.
Figure 8:
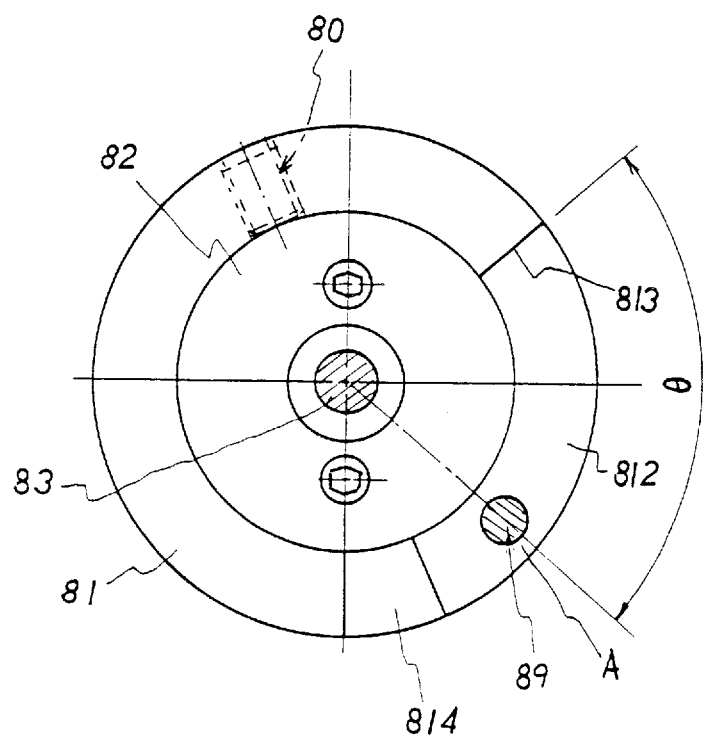
FIG. 8 is a schematic view illustrating a rotational angle of a swivel button of a preferred embodiment in accordance with the present invention.

Referring to FIGS. 4 to 8, an oil cylinder comprises a valve body 59, an oil storage chamber 55 disposed on the valve body 59, and an oil pressure chamber 56 disposed in the oil storage chamber 55. A piston chamber 591 is disposed in the valve body 59. The valve body 59 has a first half valve 59a and a second half valve 59b coupled with the first half valve 59b. The first half valve 59a and the second half valve 59b are fastened by at least a screw 7. A shaft 53 extends from the oil pressure chamber 56. A piston 57 is disposed in the piston chamber 591. An annular groove 571 is formed on the piston 57. An arc-shaped through hole 592 is formed in the valve body 59 communicating with the piston chamber 591. A trip lever 512 passes through the arc-shaped through hole 592 and inserted in the annular groove 571. An enlarged hole 597 is formed in the valve body 59 receiving a rotating post 511. The trip lever 512 is connected to the rotating post 511 eccentrically. The rotating post 511 can be rotated in the enlarged hole 597 freely. A first oil passage 593 is formed in the valve body 59 communicating with the oil storage chamber 55. A second oil passage 594 is formed in the valve body 59 communicating with the first oil passage 593. A third oil passage 596 is formed in the valve body 59 communicating with the second oil passage 594. A fourth oil passage 595 is formed in the valve body 59 communicating with the oil pressure chamber 56. A big ball 501 is placed in the third oil passage 596. A small ball 502 is placed in the second oil passage 594. A bolt 581 is inserted in the third oil passage 596. A compression spring 582 is connected to the bolt 581 and the big ball 501. A coiled spring 583 is connected to the big ball 501 and the small ball 502. The big ball 501 seals a first end of the second oil passage 594. The small ball 502 seals a second end of the second oil passage 594. The second oil passage 594 communicates with the piston chamber 591. A swivel rod 51 is connected to the rotating post 511. A V-ring oil seal 91 encloses the piston 57. An oil ring 92 is disposed between the first half valve 59a and the second half valve 59b. An oil hole 598 is formed in the valve body 59 communicating with the third oil passage 596. A first channel 599 is formed in the valve body 59 communicating with the oil hole 598. A second channel 590 is formed in the valve body 59 communicating with the first channel 599. An oil relief device 8 is disposed on the valve body 59 and inserted in the first channel 599.

The oil relief device 8 comprises an annular seat 81, a hollow disk 82 inserted in the annular seat 81, a spiral power spring 85 disposed on the hollow disk 82, a swivel button 84 enclosing the spiral power spring 85, a control rod 89 passing through the swivel button 84, a pull button 87 having a hollow post 872 inserted in the swivel button 84 and receiving a threaded end 892 of the control rod 89, an elastic member 88 disposed between the hollow post 872 and a cylinder head 891 of the control rod 89, and a needle valve 83 having a sleeve 833 passing through the hollow disk 82 and the spiral power spring 85 and inserted in the swivel button 84, an annular recess 834 receiving an oil gasket 835, a threaded portion 831 inserted in the hollow disk 82, and a cone-shaped end 832 inserted in the first channel 599.

The annular seat 81 has a threaded hole 811 receiving a stud 80, a block face 813, a recess portion 812 abutting the block face 813, an inclined groove portion 814 abutting the recess portion 812, and a center hole 815 receiving the hollow disk 82.

The hollow disk 82 has a circular central hole 822 receiving the oil gasket 835 and a circular central aperture 821 receiving the sleeve 833. The circular central aperture 821 communicates with the circular central hole 822. A plurality of fastening members 86 fasten the hollow disk 82 on the valve body 59.

The swivel button 84 has a central recess hole 841 receiving the sleeve 833, a round hole 843, and a round aperture 842 communicating with the round hole 843. The elastic member 88 encloses the threaded end 892 of the control rod 89. The threaded end 892 of the control rod 89 is inserted in the round aperture 842. The cylinder head 891 of the control rod 89 is inserted in the round hole 843. The cylinder head 891 of the control rod 89 is located on the recess portion 812.

Referring to FIGS. 6 to 8 again, the cone-shaped end 832 blocks the oil hole 598 while the swivel button 84 winds the spiral power spring 85 tightly. Then the control rod 89 is located in the position A. When the swivel button 84 is rotated from the position A to the block face 813 via a rotating angle , the swivel button 84 will rotate to the position A after the user releases the swivel button 84. Thus the oil can flow in a predetermined amount.

When the user pulls the pull button 87, the control rod 89 is released from the recess portion 812. The cone-shaped end 832 will be released from the oil hole 598. Thus the oil can flow in a large amount.

If the swivel button 84 is rotated too fast, the inclined groove portion 814 can provide a room for the control rod 89 so that the swivel button 84 can recover its original position.

Since the valve body 59 is separated into the first half valve 59a and the second half valve 59b, the perforation of holes become easilier. Thus the holes can be formed precisely with the predetermined bores.

The present invention is not limited to the above embodiment but various modification thereof may be made. Furthermore, various changes in form and detail may be made without departing from the scope of the present invention.

I claim:

1. An oil cylinder comprises:

a valve body, an oil storage chamber disposed on the valve body, an oil pressure chamber disposed in the oil storage chamber, a piston chamber disposed in the valve body, the valve body formed by a first half valve and a second half valve coupled with the first half valve, the first half valve and the second half valve fastened by at least a fastener, a shaft extending from the oil pressure chamber, a piston disposed in the piston chamber, an annular groove formed on the piston, an arc-shaped through hole formed in the valve body communicating with the piston chamber, a trip lever passing through the arc-shaped through hole and inserted in the annular groove, an enlarged hole formed in the valve body receiving a rotating post, the trip lever connected to the rotating post eccentrically, a first oil passage formed in the valve body communicating with the oil storage chamber, a second oil passage formed in the valve body communicating with the first oil passage, a third oil passage formed in the valve body communicating with the second oil passage, a fourth oil passage formed in the valve body communicating with the oil pressure chamber, a big ball placed in the third oil passage, a small ball placed in the second oil passage, a bolt inserted in the third oil passage, a compression spring connected to the bolt and the big ball, a coiled spring connected to the big ball and the small ball, the big ball sealing a first end of the second oil passage, the small ball sealing a second end of the second oil passage, the second oil passage communicating with the piston chamber, a swivel rod connected to the rotating post, a V-ring oil seal enclosing the piston, an oil ring disposed between the first half valve and the second half valve, an oil hole formed in the valve body communicating with the third oil passage, a first channel formed in the valve body communicating with the oil hole, a second channel formed in the valve body communicating with the first channel, and an oil relief device disposed on the valve body and inserted in the first channel.

2. An oil cylinder as claimed in claim 1, wherein the oil relief device comprises an annular seat, a hollow disk inserted in the annular seat, a spiral power spring disposed on the hollow disk, a swivel button enclosing the spiral power spring, a control rod passing through the swivel button, a pull button having a hollow post inserted in the swivel button and receiving a threaded end of the control rod, an elastic member disposed between the hollow post and a cylinder head of the control rod, and a needle valve having a sleeve passing through the hollow disk and the spiral power spring and inserted in the swivel button, an annular recess receiving an oil gasket, a threaded portion inserted in the hollow disk, and a cone-shaped end inserted in the first channel.

3. An oil cylinder as claimed in claim 2, wherein the annular seat has a threaded hole receiving a stud, a block face, a recess portion abutting the block face, an inclined groove portion abutting the recess portion, and a center hole receiving the hollow disk.

4. An oil cylinder as claimed in claim 2, wherein the hollow disk has a circular central hole receiving the oil gasket and a circular central aperture receiving the sleeve.

5. An oil cylinder as claimed in claim 2, wherein the control rod has a cylinder head and a threaded end.

6. An oil cylinder as claimed in claim 2, wherein the swivel button has a central recess hole receiving the sleeve, a round hole, and a round aperture communicating with the round hole.

* * * * *